United States Patent [19]

Steer et al.

[11] Patent Number: 4,963,136
[45] Date of Patent: Oct. 16, 1990

[54] COUPLING FOR ATTACHING AN OSTOMY OR POUCH TO A MEDICAL GRADE ADHESIVE PAD

[75] Inventors: Peter L. Steer, Reigate; Neil P. Wiltshire, Lingfield, both of England

[73] Assignee: E. R. Squibb & Sons, Inc., Princeton, N.J.

[21] Appl. No.: 333,055

[22] Filed: Apr. 4, 1989

[30] Foreign Application Priority Data

Apr. 15, 1988 [GB] United Kingdom ............... 8808894

[51] Int. Cl.⁵ ............................................. A61F 5/44
[52] U.S. Cl. .................................................. 604/339
[58] Field of Search ............... 604/317, 327, 332–345; 285/365–367, 407, 409, 410

[56] References Cited

U.S. PATENT DOCUMENTS

| | | | |
|---|---|---|---|
| 2,441,508 | 5/1948 | Porcell | 604/340 |
| 2,639,710 | 5/1953 | Fazio | 604/342 |
| 3,042,430 | 7/1962 | Guy | 285/365 |
| 3,076,458 | 2/1963 | Mason | 604/339 |
| 3,736,934 | 6/1973 | Hennessy | |
| 4,460,363 | 7/1984 | Steer et al. | |
| 4,834,732 | 5/1989 | Steer et al. | |
| 4,889,534 | 12/1989 | Mohiuddin et al. | 604/339 |

FOREIGN PATENT DOCUMENTS

| | | | |
|---|---|---|---|
| 0135269 | 3/1985 | European Pat. Off. | |
| 841197 | 6/1952 | Fed. Rep. of Germany | 604/337 |
| 3417183 | 5/1984 | Fed. Rep. of Germany | |
| 802823 | 9/1936 | France | |
| WO85/03427 | 8/1985 | PCT Int'l Appl. | |
| 0982961 | 2/1965 | United Kingdom | 285/365 |
| 1021145 | 3/1966 | United Kingdom | |
| 1099455 | 1/1968 | United Kingdom | |
| 1568860 | 6/1980 | United Kingdom | |
| 1579875 | 11/1980 | United Kingdom | |
| 2121902 | 3/1982 | United Kingdom | |
| 2177926 | 2/1987 | United Kingdom | |
| 2183481 | 6/1987 | United Kingdom | |
| 2193098 | 2/1988 | United Kingdom | |
| 2201345 | 9/1988 | United Kingdom | |
| 2201346 | 9/1988 | United Kingdom | |
| 2205041 | 11/1988 | United Kingdom | |
| 2215212 | 9/1989 | United Kingdom | |

OTHER PUBLICATIONS

Ostomy Catalog and Educational Training Manual, United Surgical Corp., 1968, pp. 20, 21, 27.

Primary Examiner—John D. Yasko
Assistant Examiner—Anthony M. Gutowski
Attorney, Agent, or Firm—Stephen B. Davis

[57] ABSTRACT

An ostomy coupling has two co-operating coupling elements. One is for attachment to a medical grade adhesive and the other is for attachment to an ostomy pouch. Each element is of close loop form and includes a tapering member extending around a stomal orifice. Each such member tapers in a radially outward direction and has a flat surface located in a plane at right angles to the coupling axis. The coupling also has a means of clamping which can be tightened onto the tapering members to hold them together. When held their respective flat surfaces are in face-to-face arrangement. Hence, two coupling elements can be held together and released without the application of any axial pressure forces or pulling forces to the wearer of the ostomy appliance.

4 Claims, 3 Drawing Sheets

COUPLING FOR ATTACHING AN OSTOMY OR POUCH TO A MEDICAL GRADE ADHESIVE PAD

BACKGROUND OF THE INVENTION

This invention relates to a coupling for attaching an ostomy bag or pouch to a medical grade adhesive pad, and is particularly, although not exclusively intended for couplings having a diameter in the region 75-100mm which are currently used in loop ostomy procedures.

With all ostomy appliances, it is desirable that the bag should be attachable without applying any significant pressure to the tender peristomal region of the wearer. It is particularly important with loop ostomy that the coupling by which the pouch is connected to the adhesive pad should enable fitting and removal of the bag to be accomplished with substantially no pressure or pulling forces whatsoever being applied to the peristomal region.

SUMMARY OF THE INVENTION

In accordance with the present invention, there is provided an ostomy coupling including two co-operating coupling elements, one for attachment to a pad of medical grade adhesive and the other for attachment to an ostomy pouch, in which each coupling element is of closed loop form and includes a tapering member extending completely around a stomal orifice at the center of the coupling, each such member tapering in a radially outward direction and having a flat surface located in a plane at right angles to the coupling axis, the coupling also having a means of clamping which can be tightened onto the tapering members to hold them together so that their respective flat surfaces are in face-to-face arrangement, whereby the two coupling elements can be held together and released without the application of any axial pressure forces or pulling forces to the wearer.

BRIEF DESCRIPTION OF THE DRAWINGS

The invention will be better understood from an illustrative description of a non-limiting embodiment thereof, given with references to the accompanying drawings in which.

DETAILED DESCRIPTION OF THE DRAWINGS

Figure 1:
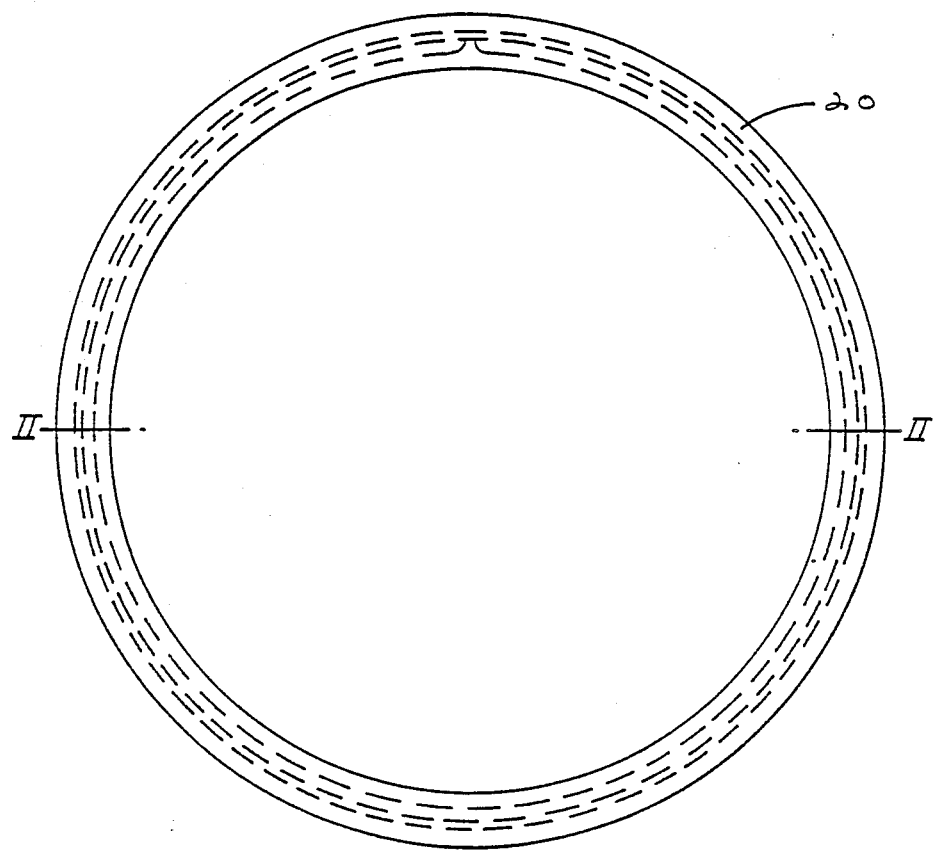
FIGS. 1 and 2 are a front elevation and half section respectively of one embodiment of coupling according to the invention, the sectional plane being II-II of FIG. 1.

In the drawings, like parts are represented by like reference numerals.

The illustrated coupling includes a bag side coupling element 20 of closed loop form which may be molded from the synthetic plastics material EVA and which is intended to co-operate with a body-side coupling element 40. The coupling is preferably a circular annulas but could be oval or any other convenient closed loop shape. For brevity of description, annular couplings are referred to herein. These two elements are held together in the assembled condition by a clamping means 60.

The bag-side coupling element 20 is annular and encircles a stomal orifice 18. It has a substantially cylindrical chute portion 22 and a radially outwardly extending flange portion 24. The flange portion 24 has a surface 26 to which may be secured an ostomy pouch or bag. The pouch or bag may be secured thereto in any conventional or convenient manner.

Figure 2:
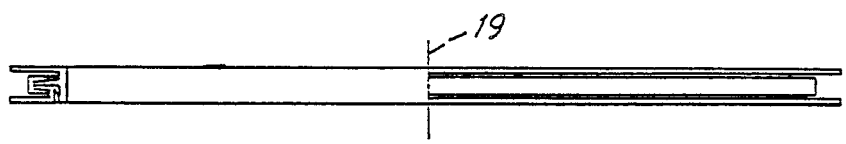
Figure 3:
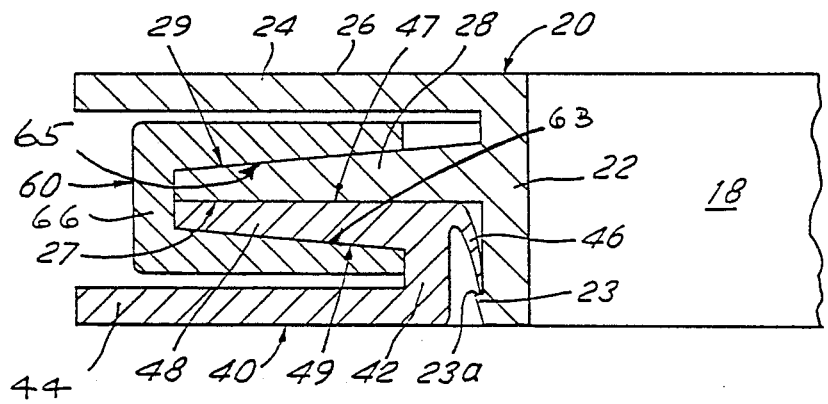
FIG. 3 is a cross-sectional view similar to FIG. 2 but on a larger scale and showing part of the periphery of an assembled coupling.
Figure 5:
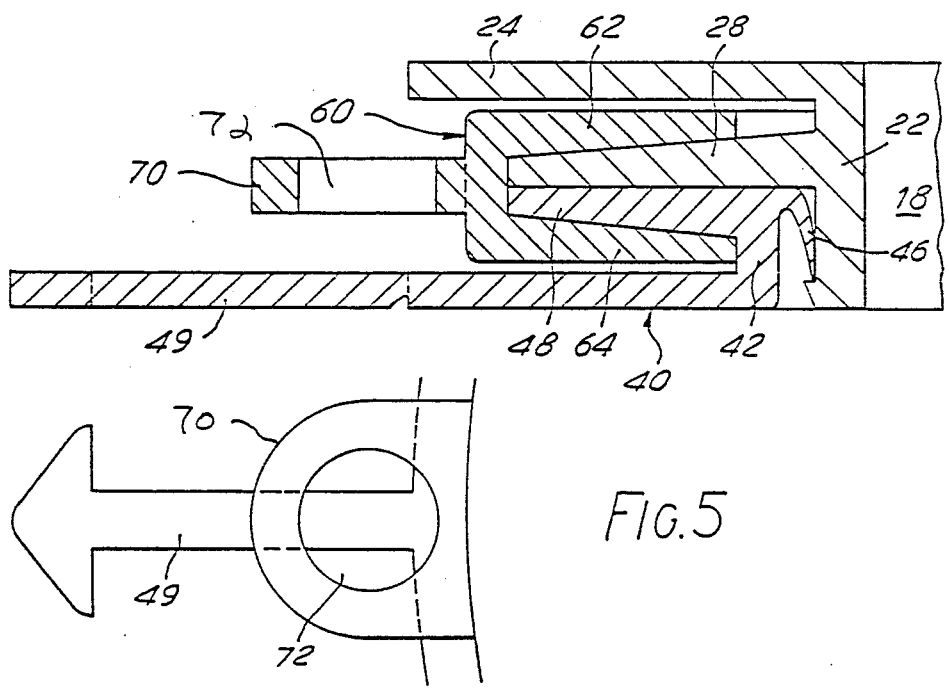
FIG. 5 is a cross-section similar to FIG. 3 but illustrating the provision of structure whereby the illustrated coupling can be readily attached or separated from a supporting belt or harness.

Also extending radially outwardly from the chute portion 22 is a tapering member 28. This is bounded by one surface 27 located in a plane perpendicular to the coupling axis 19 (FIG. 2) and a second surface 29 at an angle thereto. The surfaces 27 and 29 may include an angle of about 3-7°, preferably 5°.

At one end, the chute portion 22 has a radially outwardly projecting rim 23. This has a surface 23a substantially at right angles to the axis 19.

The body-side coupling element 40 may also be made of EVA synthetic plastics material and may be made in one molding operation. It includes a flange portion 44, an upstanding portion 42, and a radially outwardly extending member 48 which is constructed to be complimentary to the member 28 of the bag-side coupling element 20. The member 48 has one of its surfaces 47 located in a plane perpendicular to the coupling axis 19, and its surface 49 is located in a plane at about 3 to 7 degrees (preferably 5°) to the axis 19. The upstanding portion 42 has extending inwardly therefrom a flexible deflectable seal strip 46 which co-operates as indicated with the rim 23 on the chute portion 22 to provide a reliable and effective seal, preventing liquid escape. The parts may be dimensioned so that the radial distance between the outer (cylindrical) surface of the chute portion 22 and the inner (cylindrical) surface of the upstanding portion 44 is around 0.02 inches, i.e. substantially 0.5 mm.

Figure 4:
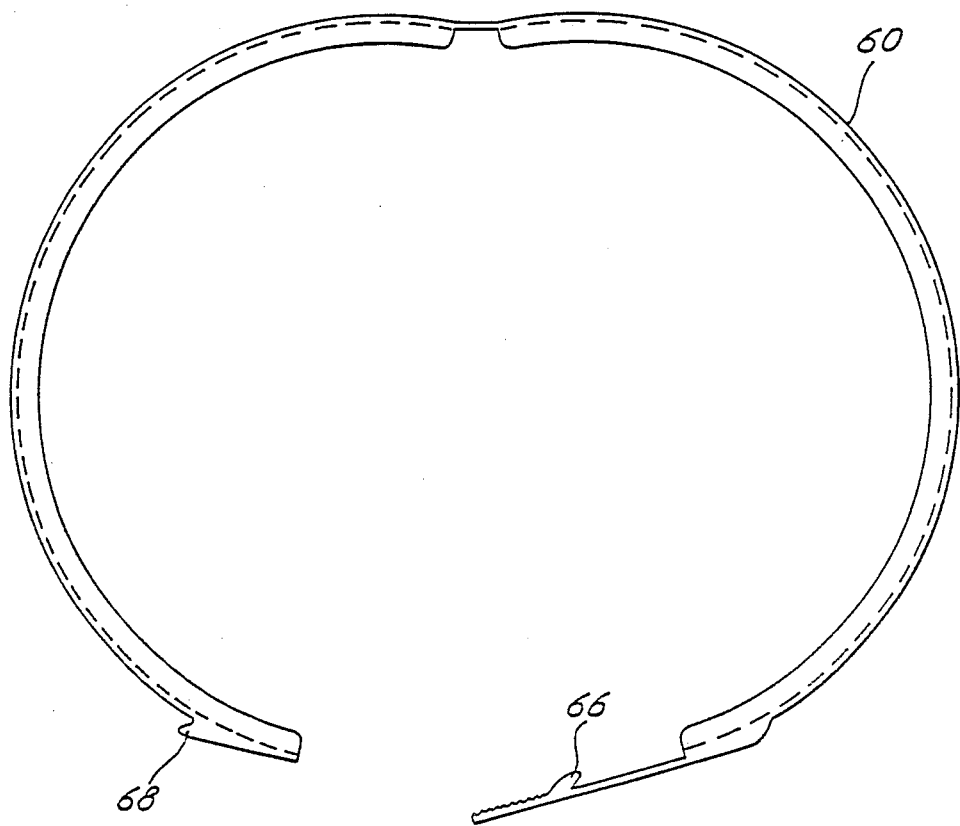
FIG. 4 is a front view of a clamping means forming part of the illustrated coupling.

The clamping means 60 shown in FIG. 4 comprises an openable and closable ring-like clamp having a U-shaped channel seen in cross-section. The clamping means 60 has a pair of wall 62, 64 and a base 66. The inner facing surfaces 63, 65 of the walls are angled inwardly at an angle substantially equal to the angle of the surfaces 29 and 49.

In order to clamp the coupling elements 20 and 40 securely together, the clamping ring 60 is placed in encircling relationship so that its walls embrace the members 28 and 48 and then the ring is closed by hooking the hook 66 over the catch 68.

At two locations diametrically opposite to one another, the clamping means 60 has a radially extending lug 70 with a hole 72 therein. The holes at opposite ends of a diameter are to permit attachment of a belt or harness, if desired. As an alternative arrangement, or in addition, at two locations around the periphery of the coupling element 40, preferably diametrically opposite to one another, the coupling element 40 may be provided with integral radially extending arrowheads 49. These are provided for cooperation with a belt or harness.

In use, the bag-side coupling element with bag attached thereto can be brought towards the body-side coupling element, attached to the body of the wearer by the medical grade adhesive pad, until the faces 47 and 27 come into contact. The clamp ring 60 is then fitted around the peripheral edges of the members 28 and 48, and closed by engaging its hook 66 over its catch 68. The ring 60 then holds the two coupling parts together, but application of this clamping pressure due to the tapering shape of the members 28 and 48 and the configuration of the U-shaped channel does not involve any axial forces on the tender peristomal area.

It will be appreciated that the invention can be carried out in other ways and hence it is not desired to limit the invention by the details particularly described and illustrated herein.

What is claimed is:

1. An ostomy coupling includes two cooperating coupling elements of closed loop form extending completely around a stomal orifice at the center of the coupling, one for attachment to a pad of medical grade adhesive and the other for attachment to an ostomy pouch, one of said coupling elements including a substantially cylindrical chute member extending around said stomal orifice and the other including an upstanding portion with a flexible deflectable seal strip which engages the radially outer wall of said chute member to provide a seal when the coupling elements are coupled together, in which each coupling element includes a tapering member, each such member tapering in a radially outward direction from, and formed integrally with, said chute member and said upstanding portion, respectfully, and having a flat surface located in a plane at right angles to the coupling axis, the coupling also having a means of clamping which can be tightened onto the tapering members to hold them together so that their respective flat surfaces are in face-to-face arrangement, whereby the two coupling elements can be held together and released without the application of any axial pressure forces or pulling forces to the wearer, said clamping means comprising a U-shaped channel in which the inside walls of the U-shaped channel are tapered to be complimentary to the tapered surfaces of the tapering members.

2. A coupling according to claim 1 in which the clamping means is closable by a hook and catch structure.

3. A coupling according to claim 1 including means whereby a belt can be attached to the clamping means or to one of the coupling elements.

4. A coupling according to claim 2 including means whereby a belt can be attached to the clamping means or to one of the coupling elements.

* * * * *